United States Patent [19]

McKnight et al.

[11] Patent Number: 5,618,693
[45] Date of Patent: Apr. 8, 1997

[54] INTERLEUKIN-2 SIGNAL TRANSDUCERS AND BINDING ASSAYS

[75] Inventors: Steven L. McKnight; Jinzhao Hou; Ulrike Schindler, all of So. San Francisco, Calif.

[73] Assignee: Tularik, Inc., South San Francisco, Calif.

[21] Appl. No.: 393,333

[22] Filed: Feb. 23, 1995

[51] Int. Cl.$^6$ .............................. C12P 21/06; C12N 5/00; C12N 15/12; C12N 15/63

[52] U.S. Cl. ................ 435/69.1; 435/320.1; 435/252.33; 435/325; 435/372; 536/23.5

[58] Field of Search ....................... 536/23.5; 435/320.1, 435/240.1, 240.2, 69.1

[56] References Cited

PUBLICATIONS

Beadling et al., "Activation of JAK Kinases and STAT Proteins by Interleukin–2 and Interferon α, but not the T Cell Antigen Receptor, in human T Lymphocytes", *The EMBO Journal* 13(23):5605–5615 (1994).

Gilmour and Reich, "Receptor to Nucleus Signaling by Prolactin and Interleukin 2 via Activation of Latent DNA–binding Factors", *Proc. Natl. Acad. Sci. USA* 91:6850–6854 (1994).

Wakao et al., "Mammary Gland Factor (MGF) is a Novel Member of the Cytokine Regulated Transcription Factor Gene Family and Confers the Prolactin Response" *The EMBO Journal* 13(9):2182–2191 (1994).

*Primary Examiner*—Mindy Fleisher
*Assistant Examiner*—Terry A. McKelvey
*Attorney, Agent, or Firm*—Flehr Hohbach Test Albritton & Herbert LLP

[57] ABSTRACT

The invention provides methods and compositions relating to interleukin 2 signal transducers, particularly an isolated human signal transducer and activator of transcription 5 (hStat 5), or a fragment thereof having an hStat 5-specific binding affinity, nucleic acids encoding hStat 5, which nucleic acids may be part of hStat 5-expression vectors and may be incorporated into a recombinant cell, agents which selectively bind hStat 5 or hStat 5 intracellular binding targets, or disrupt the binding of hStat 5 to such intracellular targets, methods of making such agents and hStat 5-specific binding targets in the form of cell surface proteins and nucleic acids. An hStat 5 drug screening assay involves forming mixtures of an hStat 5, an intracellular hStat 5 binding target, and a prospective agent at different concentrations. The mixtures are incubated to permit the binding of the intracellular hStat 5 binding target to the hStat 5 and the mixtures are then analyzed for the presence of such binding. A difference in such binding between the first and second mixtures indicates that the agent is capable of modulating the binding of hStat 5 to an intracellular hStat 5 binding target.

28 Claims, No Drawings

INTERLEUKIN-2 SIGNAL TRANSDUCERS AND BINDING ASSAYS

INTRODUCTION

1. Field of the Invention

The field of this invention is human interleukin-2 signal transducers.

2. Background

Identifying and developing new pharmaceuticals is a multibillion dollar industry in the U.S. alone. Gene specific transcription factors provide a promising class of targets for novel therapeutics directed to these and other human diseases. Urgently needed are efficient methods of identifying pharmacological agents or drugs which are active at the level of gene transcription. Methods amenable to automated, cost-effective, high throughput drug screening have immediate application in a broad range of domestic and international pharmaceutical and biotechnology drug development programs.

Immunosuppression is therapeutically desirable in a wide variety of circumstances including transplantation, allergy and other forms of hypersensitivity, autoimmunity, etc. Cyclosporin, a widely used drug for effecting immunosuppression, is believed to act by inhibiting a calcineurin, a phosphatase which activates certain transcription factors. However, because of side effects and toxicity, clinical indications of cyclosporin (and the more recently developed FK506) are limited.

Interleukin-2 (IL-2) is an immunomodulatory cytokine secreted by activated T lymphocytes. IL-2 stimulates the proliferation and differentiated function of hematopoietic cells including T cells, B cells, NK cells, LAK cells, monocytes, macrophages and oligodendrocytes. Specifically, IL-2 is the major autocrine growth factor for T lymphocytes regulating the magnitude of T cell-dependent immune responses; IL-2 stimulates the growth of NK cells and enhances their cytolytic function; and IL-2 stimulates growth and antibody synthesis in B cells. As such, IL-2 signal transduction provides an important target for pharmaceutical intervention in the immune system. Accordingly, it is desired to identify agents which specifically interfere with transduction of IL-2 signalling. Unfortunately, the reagents necessary for the development of high-throughput screening assays for such therapeutics are unavailable.

Relevant Literature

The subunit structure of the IL-2 receptor is described in Cosman et al., 1984; Leonard et al., 1984; Nikaido et al., 1984; Hatakeyama et al., 1989; Takeshita et al., 1992; Voss et al., 1993. The IL-2Ra chain appears to be uniquely dedicated to IL-2 response, whereas the IL-2Rb and IL-2Rg chains are commonly used by other cytokine receptors (Kondo et al., 1993; Noguchi et al., 1993; Giri et al., 1994). On its own, IL-2Ra is capable of low affinity binding to IL-2. High affinity binding and biological response to IL-2 requires, however, association of IL-2Ra with the IL-2Rb and IL-2Rg chains of the receptor (Minamoto et al., 1990; Takeshita et al., 1990). Moreover, functional signaling via the IL-2 receptor is dependent upon the integrity of the intracellular domains of IL-2Rb and IL-2R9 (Kawahara et al., 1994; Nakamura et al., 1994; Nelson et al., 1994). Upon stimulation by IL-2, receptor-bearing cells have been shown to activate the Jak 1 and Jak 3 tyrosine kinases (Boussiotis et al., 1994; Miyazaki et al., 1994; Russell et al., 1994). IL-2 has also been observed to activate an otherwise latent DNA binding activity bearing properties related to Stat proteins (Gilmour and Reich, 1994; Beadling et al., 1994).

Wakao, et al. (1994) disclose a sheep protein, mammary gland factor (MGF) with sequence similarity to hStat 5.

SUMMARY OF THE INVENTION

The invention provides methods and compositions relating to interleukin-2 signal transducers. In one embodiment, the invention provides isolated human signal transducer and activator of transcription 5 (hStat 5), or a fragment thereof having an hStat 5-specific binding affinity. The invention provides nucleic acids encoding the subject hStat 5 and hStat 5 fragments, which nucleic acids may be part of hStat 5-expression vectors and may be incorporated into a recombinant cell. The invention provides agents which selectively bind hStat 5 or hStat 5 intracellular binding targets, or disrupt the binding of hStat 5 to such intracellular targets, and methods of making such agents. The invention also provides specific hStat 5 binding targets in the form of cell surface proteins and nucleic acids.

The subject hStat 5 and hStat 5 fragments and find particular use in screening assays for agents or lead compounds for agents useful in the diagnosis, prognosis or treatment of disease, particularly disease associated with undesirable cell growth, differentiation and/or cytokine signal responsiveness. One such assay involves forming mixtures of an hStat 5, an intracellular hStat 5 binding target, and a prospective agent at different concentrations. Typically, one mixture is a negative control (i.e. the agent concentration is zero). The mixtures are incubated to permit the binding of the intracellular hStat 5 binding target to the hStat 5 and the mixtures are then analyzed for the presence of such binding. A difference in such binding between the first and second mixtures indicates that the agent is capable of modulating the binding of hStat 5 to an intracellular hStat 5 binding target.

DETAILED DESCRIPTION OF THE INVENTION

The invention provides methods and compositions relating to human interleukin-2 signal transducers including hStat 5. A cDNA encoding hStat 5 and its translation product are shown in SEQ ID NOS:1 and 2, respectively.

The subject hStat 5 fragments have one or more hStat 5-specific binding affinities which distinguish other Stats and Stat-related proteins such as MGF, including the ability to specifically bind at least one natural human intracellular hStat 5-specific binding target or a hStat 5-specific binding agent such as a hStat 5-specific antibody or a hStat 5-specific binding agent identified in assays such as described below. Accordingly, the specificity of hStat 5 fragment specific binding agents is confirmed by ensuring non-crossreactivity with other stats. Furthermore, preferred hStat 5 fragments are capable of eliciting an antibody capable of distinguishing hStat 5 from other Stats and MGF. Methods for making immunogenic peptides through the use of conjugates, adjuvants, etc. and methods for eliciting antibodies, e.g. immunizing rabbits, are well known.

Exemplary natural intracellular binding targets include nucleic acids which comprise one or more hStat 5 DNA binding sites such as the interleukin response element of the gene encoding FcγRI, cell surface proteins such as the hStat 5 binding domain the IL-2 receptor and phosphotryrosine peptide fragments thereof, protein kinases such as Janus tyrosine kinases, transcription factors such as those comprising the transcription initiation complex, etc., and fragments of such targets which are capable of hStat 5-specific binding. Other natural hStat 5 binding targets are readily identified by screening cells, membranes and cellular extracts and fractions with the disclosed materials and methods and by other methods known in the art. For example, two-hybrid screening using hStat 5 fragments are used to identify intracellular targets which specifically bind such fragments. Preferred hStat 5 fragments retain the ability to specifically bind at least one of an hStat 5 DNA binding site and an intracellular domain of an IL-2 receptor subunit. For example, using a strategy analagous to that described in Hou et al. (1994) Science 265:1701–1706 phosphotyrosine peptides proximal to the carboxyl termixus of the IL-2Rβ chain are shown to inhibit hStat5 DNA binding. IL-2Rβ variants lacking these two peptides are found to lose the ability to activate Stat proteins. Convenient ways to verify the ability of a given hStat 5 fragment to specifically bind such targets include in vitro labelled binding assays such as described below, and EMSAs.

A wide variety of molecular and biochemical methods are available for generating and expressing hStat 5 fragments, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, N.Y., N.Y., 1992) or that are otherwise known in the art. For example, hStat 5 or fragments thereof may be obtained by chemical synthesis, expression in bacteria such as *E. coli* and eukaryotes such as yeast or vaccinia or baculovirus-based expression systems, etc., depending on the size, nature and quantity of the hStat 5 or fragment. The subject hStat 5 fragments are of length sufficient to provide a novel peptide. As used herein, such peptides are at least 5, usually at least about 6, more usually at least about 8, most usually at least about 10 amino acids. hStat 5 fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

The subject hStat 5 fragments maintain binding affinity of not less than six, preferably not less than four, more preferably not less than two orders of magnitude less than the binding equilibrium constant of a full-length native hStat 5 to the binding target under similar conditions. Particular hStat 5 fragments or deletion mutants are shown to function in a dominant-negative fashion. Particular hStat 5 fragments containing tyrosine residue 694 are also shown to prevent tyrosine phosphorylation of hStat 5 thereby inhibiting hStat 5 activity. Such fragments provide therapeutic agents, e.g. when delivered by intracellular immunization—transfection of susceptible cells with nucleic acids encoding such mutants.

The claimed hStat 5 and hStat 5 fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample.

The invention provides hStat 5-specific binding agents, methods of identifying and making such agents, and their use in diagnosis, therapy and pharmaceutical development. For example, hStat 5-specific agents are useful in a variety of diagnostic applications, especially where disease or disease prognosis is associated with immune disfunction resulting from improper expression of hStat 5. Novel hStat 5-specific binding agents include hStat 5-specific antibodies; novel nucleic acids with sequence similarity to that of the FcγγRI receptor promoter as described below; isolated IL-2 receptor subunit domains; other natural intracellular binding agents identified with assays such as one- and two-hybrid screens; non-natural intracellular binding agents identified in screens of chemical libraries, etc.

Generally, hStat 5-specificity of the binding target is shown by binding equilibrium constants. Such targets are capable of selectively binding a hStat 5, i.e. with an equilibrium constant at least about $10^4 M^{-1}$, preferably at least about $10^6 M^{-1}$, more preferably at least about $10^8 M^{-1}$. A wide variety of cell-based and cell-free assays may be used to demonstrate hStat 5-specific binding. Cell based assays include one and two-hybrid screens, mediating or competitively inhibiting hStat 5-mediated transcription, etc. Preferred are rapid in vitro, cell-free assays such as mediating or inhibiting hStat 5-protein (e.g. hStat 5-IL-2 receptor subunit binding), hStat 5-nucleic acid binding, immunoassays, etc. Other useful screening assays for hStat 5/hStat 5 fragment-target binding include fluorescence resonance energy transfer (FRET), electrophoretic mobility shift analysis (EMSA), etc.

The invention also provides nucleic acids encoding the subject hStat 5 and hStat 5 fragments, including fragments comprising at least one of amino acid sequence ATQLQK (SEQ ID NO:2, residues 91–96): YDRCPLELV (SEQ ID NO:2, residues 98–106); NNCSSP (SEQ ID NO:2, residues 124–129); QQLAGNGG (SEQ ID NO:2. residues 259–266); NGGPPEG (SEQ ID NO:2, residues 264–270); NASADAG (SEQ ID NO:2, residues 708–714); SATYMDQAP (SEQ ID NO:2, residues 717–725); SPAVCPQAP (SEQ ID NO:2, residues 726–734); YNMYPQNPD (SEQ ID NO:2, residues 735–743); HVLDQDOEF (SEQ ID NO:2, residues 744–752); DLDETMDVA (SEQ ID NO:2, residues 753–761); VEELLRR (SEQ ID NO:2, residues 764–770); MDSLDSRLS (SEQ ID NO:2, residues 772–780); and FTSAROSLS (SEQ ID NO:2, residues 786–794), which nucleic acids may be part of hStat 5-expression vectors and may be incorporated into recombinant cells for expression and screening, transgenic animals for functional studies (e.g. the efficacy of candidate drugs for disease associated with expression of a hStat 5), etc. In addition, the invention provides nucleic acids sharing substantial sequence similarity with that of one or more wild-type hStat 5 nucleic acids. Substantially identical or homologous nucleic acid sequences hybridize to their respective complements under high stringency conditions, for example, at 55° C. and hybridization buffer comprising 50% formamide in 0.9M saline/0.09M sodium citrate (SSC) buffer and remain bound when subject to washing at 55° C. with the SSC/formamide buffer. Where the sequences diverge, the differences are preferably silent, i.e. or a nucleotide change providing a redundant codon, or conservative, i.e. a nucleotide change providing a conservative amino acid substitution.

The subject nucleic acids find a wide variety of applications including use as hybridization probes, PCR primers, therapeutic nucleic acids, etc. for use in detecting the presence of hStat 5 genes and gene transcripts, for detecting or amplifying nucleic acids with substantial sequence similarity such as hStat 5 homologs and structural analogs, and for gene therapy applications. Given the subject probes, materials and methods for probing CDNA and genetic libraries and recovering homologs are known in the art. Preferred libraries are derived from human immune cells, especially CDNA libraries from differentiated and activated human lymphoid cells. In one application, the subject nucleic acids find use as hybridization probes for identifying hStat 5 cDNA homologs with substantial sequence similarity. These homologs in turn provide additional Stats and Stat fragment for use in binding assays and therapy as described herein. hStat 5 encoding nucleic acids also find applications in gene therapy. For example, nucleic acids encoding dominant-negative hStat 5 routants are cloned into a virus and the virus used to transfect and confer disease resistance to the transfected cells.

Therapeutic hStat 5 nucleic acids are used to modulate, usually reduce, cellular expression or intracellular concentration or availability of active hStat 5. These nucleic acids are typically antisense: single-stranded sequences comprising complements of the disclosed hStat 5 nucleic acids. Antisense modulation of hStat 5 expression may employ hStat 5 antisense nucleic acids operably linked to gene regulatory sequences. Cell are transfected with a vector comprising an hStat 5 sequence with a promoter sequence oriented such that transcription of the gene yields an antisense transcript capable of binding to endogenous hStat 5 encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a hStat 5 or hStat 5 fragment may be administered to the target cell, in or temporarily isolated from a host, at a concentration that results in a substantial reduction in hStat 5 expression. For gene therapy involving the transfusion of hStat 5 transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The subject nucleic acids are often recombinant, meaning they comprise a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of hStat 5 modulatable cellular function, particularly hStat 5 mediated interleukin signal transduction. Generally, these screening methods involve assaying for compounds which interfere with hStat 5 activity such as hStat 5-IL-2 receptor binding, hStat 5-DNA binding, etc. The methods are amenable to automated, cost-effective high throughput drug screening and have immediate application in a broad range of domestic and international pharmaceutical and biotechnology drug development programs.

Target therapeutic indications are limited only in that the target cellular function (e.g. gene expression) be subject to modulation, usually inhibition, by disruption of the formation of a complex (e.g. transcription complex) comprising a hStat 5 or hStat 5 fragment and one or more natural hStat 5 intracellular binding targets. Since a wide variety of genes are subject to hStat 5 regulated gene transcription, target indications may include viral, bacterial and fungal infections, metabolic disease, genetic disease, cell growth and regulatory disfunction, such as neoplasia, inflammation, hypersensitivity, etc. Frequently, the target indication is related to either immune dysfunction or selective immune suppression.

A wide variety of assays for binding agents are provided including labelled in vitro protein-protein and protein-DNA binding assay, electrophoretic mobility shift assays, immunoassays for protein binding or transcription complex formation, cell based assays such as one, two and three hybrid screens, expression assays such as transcription assays, etc. For example, three-hybrid screens are used to rapidly examine the effect of transfected nucleic acids, which may, for example, encode combinatorial peptide libraries or antisense molecules, on the intracellular binding of hStat 5 or hStat 5 fragments to intracellular hStat 5 targets. Convenient reagents for such assays (e.g. GAL4 fusion partners) are known in the art.

hStat 5 or hStat 5 fragments used in the methods are usually added in an isolated, partially pure or pure form and are typically recombinantly produced. The hStat 5 or fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural intracellular hStat 5 binding target such as an IL-2 receptor subunit domain or a nucleic acid comprising a sequence which shares sufficient sequence similarity with a gene or gene regulatory region to which the native hStat 5 naturally binds to provide sequence-specific binding of the hStat 5 or hStat 5 fragment. Such a nucleic acid may further comprise one or more sequences which facilitate the binding of a second transcription factor or fragment thereof which cooperatively binds the nucleic acid with the hStat 5 (i.e. at least one increases the affinity or specificity of the DNA binding of the other). While native binding targets may be used, it is frequently preferred to use portions (e.g. peptides, nucleic acid fragments) or analogs (i.e. agents which mimic the hStat 5 binding properties of the natural binding target for the purposes of the assay) thereof so long as the portion provides binding affinity and avidity to the hStat 5 conveniently measurable in the assay. Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art.

Where used, the nucleic acid portion bound by the peptide(s) may be continuous or segmented and is usually linear and double-stranded DNA, though circular plasmids or other nucleic acids or structural analogs may be substituted so long as hStat 5 sequence-specific binding is retained. In some applications, supercoiled DNA provides optimal sequence-specific binding and is preferred. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp. Additional nucleotides may be used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the hStat 5 specifically binds the cellular binding target, portion or analog. The mixture components can be added in any order that provides for the requisite bindings. Incubations may be performed at any temperature which facilitates optimal binding, typically between 4 and 40° C., more commonly between 15 and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the hStat 5 and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. For cell based assays such as one, two, and three hybrid screens, the transcript resulting from hStat 5-target binding usually encodes a directly or indirectly detectable product (e.g. galactosidase activity, luciferase activity, etc.). For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit hStat 5-target binding or transcription complex formation provide valuable reagents to the pharmaceutical industries for animal and human trials.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microliter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing the subject hStat 5 and hStat 5 fragments.

The subject hStat 5 and hStat 5 fragments and nucleic acids provide a wide variety of uses in addition to the in vitro binding assays described above. For example, cell-based assays are provided which involve transfecting an IL-2 receptor subunit or functional fragment thereof expressing cell with an hStat 5 inducible reporter such as luciferase. Agents which modulate hStat 5 mediated cell function are then detected through a change in the reporter. Another approach is a transient expression assay. In this method, cells are transfected with one or more constructs encoding in sum, a polypeptide comprising a portion of hStat 5 capable of selectively binding an natural IL-2 receptor target and a reporter under the transcriptional control of a promoter comprising a functional hStat 5 binding site. The cell may advantageously also be cotransfected with a construct encoding an hStat 5 activator, usually a tyrosine kinase, particularly a Jak kinase.

The subject compositions also provide therapeutic applications. For example, hStat 5 peptides comprising tyrosine residue 694 or IL-2 receptor peptides capable of selectively binding said hStat 5 peptides find use in treating disease associated with undesirable cell growth, differentiation, particularly immune cell differentiation, and cytokine, particularly interleukin, more particularly IL-2, responsiveness. For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration of will generally be in the range of about 100 to 500 µg/ml in the dose administered. Other additives may be included, such as stabilizers, bactericides, etc. These additives will be present in conventional amounts.

The following examples are offered by way of illustration and not by way of limitation.

EXPERIMENTAL

Peripheral blood lymphocytes (PBLs) isolated from human plasma were cultured in the presence (hereafter designated "stimulated") or absence (hereafter designated "resting") of PHA for three days. PHA stimulated cells were washed and cultured for an additional 12 hours in the absence of PHA. Both cultures were exposed to varying concentrations of recombinant IL-2 for 15 minutes then used to prepare nuclear extracts (Experimental Procedures). Gel mobility shift assays were performed using a DNA probe derived from the promoter of the gene encoding the FcgRI immunoglobulin receptor that is known to bind Stat proteins avidly (Kotanides and Reich, 1993).

Nuclear extracts prepared from both PHA-stimulated and resting PBLs contained three DNA binding activities capable of forming stable complexes with the FcgRI probe. The slowest migrating complex, designated P1, was eliminated when challenged with specific competitor DNA, yet was insensitive to competition by a mutated derivative of the FcgRI probe (Experimental Procedures). The two more rapidly migrating complexes were insensitive to challenged with specific competitor DNA and therefore deemed nonspecific (NS). IL-2 treatment of both PHA-stimulated and resting PBL cultures failed to substantially alter the abundance of the activities responsible for generating either the P1 or NS complexes. Cytokine treatment did, however, lead to the appearance of a DNA binding activity, designated P2, that was sensitive to competition by the FcgRI probe. Optimal activation of the P2 complex in resting PBLs required 30 ng/ml IL-2. PHA stimulated PBLs contained peak levels of this activity when stimulated at the lowest dose of IL-2 tested (3 ng/ml).

A transformed human lymphocyte cell line termed YT (Yodoi et al., 1985) was identified as a potential source for purification of IL-2 induced transcription factors. Nuclear extracts prepared from uninduced YT cells were observed to contain several activities capable of binding to the FcgRI probe. Competition assays revealed the slowest migrating complex (Y1) to be specific and the more rapidly migrating complexes to be non-specific (NS). None of the three activities appeared to change as a function of IL-2 presentation. Following exposure for 15 minutes to recombinant IL-2, however, two new DNA binding activities were observed. One activity, designated Y2, was induced in response to intermediate concentrations of IL-2 (10–30 ng/ml). The other, designated Y3, required exposure to higher concentration of cytokine (30–100 ng/ml). Both of the IL-2 induced DNA binding activities obtained from YT cells were sensitive to specific competitor DNA, yet insensitive to the mutated derivative of the FcgRI probe. Two observations indicated that the constitutive (P1) and IL-2 induced (P2) complexes obtained from PBLs might correspond, respectively, to the IL-2 induced complexes obtained from YT cells (Y2 and Y3). First, they co-migrated when analyzed by the gel mobility shift assay (P1=Y3 and P2=Y2). Second, the P2 and Y2 complexes were induced in resting PBLs and YT cells with similar dose dependencies (10–30 ng/ml).

Having obtained provisional evidence that PBLs and YT cells induce similar DNA binding activities in response to IL-2 we set out to purify the polypeptides specifying these activities. Nuclear extracts were prepared from 40 liters of YT cells that had been exposed for 15 minutes to 30 ng/ml of recombinant IL-2. A purification scheme involving ammonium sulfate precipitation followed by S-Sepharose, DNA affinity and Q-Sepharose chromatography (Experimental. Procedures) led to the isolation of a complex group of polypeptides that migrated on denaturing polyacrylamide gels in the range of 85–100 kD. Western blotting assays using anti-phosphotyrosine antibodies gave evidence that many, if not all, of these proteins were tyrosine phosphorylated.

The proteins purified according to procedures outlined in the preceding paragraph were cleaved with lysine-C and resulting peptide fragments were fractionated by reversed phase capillary high-performance liquid chromatography (HPLC). Partial amino acid sequences were resolved for six peptides (Experimental Procedures). When compared with a data base of known protein sequences, two of the sequenced peptides were found to correspond to Stat 1 (Schindler et al., 1992) and four to Stat 3 (Akira et al., 1994).

Apparently, YT cells induced with IL-2 contain activated Stat 1 and Stat 3. Recall, however, that at least three distinct Stat-like complexes were observed in YT nuclear extracts. One such complex, termed Y1, was present irrespective of IL-2 presentation. The other two, designated Y2 and Y3, were induced, respectively, by intermediate and relatively high levels of recombinant IL-2.

In order to determine the molecular identities of the three complexes, antibodies specific to Star 1 and Star 3 were incubated with nuclear extracts derived from uninduced and IL-2 induced YT cells. Antibodies specific to Stat 1 did not affect the Y1 complex formed between uninduced YT nuclear extract and the FcgRI probe. However, when incubated with extracts prepared from cells exposed to 30 ng/ml IL-2, the Stat-1 antibody altered the mobility of the most rapidly migrating, IL-2 induced complex (Y3). Compared with untreated extracts, or extracts incubated with control antibodies, those incubated with antibodies to Stat 1 resulted in a protein:DNA complex that migrated at a significantly retarded (supershifted) rate. Identical results were observed with nuclear extracts prepared from PBLs induced with 30 ng/ml IL-2. That is, the P1 complex was selectively supershifted by Stat 1 antibodies. We therefore conclude that Stat 1 was activated in YT cells in response to relatively high concentrations of IL-2. PBLs also contain Stat 1 that, at least in the case of the PHA-stimulation, was marginally induced by IL-2.

Antibodies to Stat 3 were also tested using nuclear extracts prepared from uninduced YT cells, as well as YT cells and PBLs that had been exposed for 15 minutes to 30 ng/ml IL-2. In this case we observed a distinctive alteration in the migration of the Y1 complex formed by YT nuclear extracts, irrespective of exposure to IL-2. Antibodies to Stat 3 did not affect the abundance or migration of DNA binding activities derived from IL-2 induced PBLs, irrespective of stimulation by PHA. According to these observations, we conclude that active Stat 3 is constitutively present in YT cells and is not further stimulated by IL-2 in either YT cells or PBLs.

The observations outlined thus far provide a molecular link between Stat 1 and a protein:DNA complex induced in YT cells by relatively high levels of IL-2 (designated Y3), as well as link between Stat 3 and a complex present in uninduced YT cells (designated Y1). Left unresolved, however, was the molecular nature of the Y2 activity induced in YT cells by intermediate concentrations of IL-2. A co-migrating DNA:protein complex, designated P2, was also induced by intermediate concentrations of IL-2 in resting PBLs, and by very low concentrations of IL-2 in PHA stimulated PBLs. In order to resolve the identity of the polypeptides specifying this activity, the complex of Stat proteins purified from YT cells was purged of Stat 1 and Stat 3 by immunodepletion.

Protein purified from 20 liters of IL-2 induced YT cells was incubated sequentially with antibodies specific to Stat 1 and Stat 3 and Sepharose beads linked to protein-A (Experimental Procedures). Load, flow-through, wash and bound fractions were then analyzed by SDS gel electrophoresis and subsequent staining using Coomassie blue as well as antibodies to phosphotyrosine, Stat 1 and Stat 3. The resulting staining patterns revealed effective depletion of Stat 1 and Stat 3. Both Coomassie and anti-phosphotyrosine staining indicated, however, that the flow through fraction retained Stat-like proteins. The three most prominent polypeptides remaining following immunodepletion were excised and individually digested with lysine-C. Resulting peptide fragments were separated by reversed phase capillary HPLC and subjected to partial amino acid sequence analysis.

The largest of the three polypeptide bands, which migrated with an apparent molecular mass of 98 Kd, yielded three peptide sequences, all of which matched the sequence of a previously characterized protein variously termed mammary gland factor (MGF) or Stat 5 (wakao et al., 1994). Two of the peptides yielded unambiguous sequences of 10 and 14 residues. Both of these sequences were identical to segments of MGF/Stat 5. The third peptide, designated peak #12, did not contain an identifiable amino acid residue in the fifth Edman degradation cycle. Ten of the eleven residues of this sequence did, however, match perfectly with a segment located close to the carboxyl terminus of MGF/Stat 5. The unidentified residue of this peptide corresponded to tyrosine residue 694 of MGF/Stat 5, which has been identified as the substrate for Jak-mediated phosphorylation (Gouilleux et al., 1994).

Reasoning that the ambiguity observed upon amino acid sequence analysis of this third peptide might reflect the fact the fifth residue was phosphorylated on tyrosine, and therefore not extracted by the non-polar solvent used to extract the phenylthiohydantion during Edman degradation (Aebersold et al., 1991; Yip and Hutchens, 1992), we performed matrix-assisted laser ionization desorption/ionization (MALDI) mass spectrometry analysis. The observed mass of the peptide (1,297.0±2 daltons) corresponded very closely to that predicted for the tyrosine phosphoform of the sequence AVDGYVKPQIK (SEQ ID NO: 2, residues 690–700) (1,298.4 daltons). Given that the affinity chromatographic step of our purification procedure selects for the active form of Stat proteins (Hou et al., 1994), and that the Stat activation cycle entails tyrosine phosphorylation (Darnell et al., 1994), it is not surprising that the Stat protein activated in IL-2 induced YT cells is tyrosine phosphorylated.

Peptide sequence analysis of two smaller Stat-like proteins remaining after immunodepletion (migrating with apparent masses of 94 and 88 Kd) also yielded sequences identical to MGF/Stat 5. We thus conclude that the sample of proteins purified from IL-2 induced YT cells, following depletion of Stat 1 and Stat 3, is largely composed of polypeptides related to MGF/Stat 5. Moreover, the three predominant species (98, 94 and 88 Kd) all appear to be tyrosine phosphorylated on the same residue. We conclude that activation of this family of proteins by IL-2 in human YT cells entails tyrosine phosphorylation at the same position as prolactin-mediated activation of MGF/Stat 5 (Gouilleux et al., 1994).

The relevance of the aforementioned finding may be signified by the fact that prolactin and IL-2 activate different Jak kinases. Two recent studies have provided evidence that prolactin activates Jak 2 (Gilmour and Reich, 1994; Rui et al., 1994). In contrast, IL-2 has been shown to activate Jak 1 and Jak 3 (Boussiotis et al., 1994; Miyazaki et al., 1994; Russell et al., 1994). Having found that MGF and hStat 5 are tyrosine phosphorylated on the same residue (694), we conclude that the specificity of activation is not controlled by Jak kinases, but rather that the functional Jak employed in Stat activation is dictated by the intracellular domain of the relevant receptor. In the case of the prolactin receptor, MGF activation is mediated by Jak 2 due, presumably, to the affinity of Jak 2 to the intracellular domain of the prolactin receptor. In contrast, hStat 5 is activated by Jak 1 and/or Jak 3 by virtue of their affinity to one or more chains of the IL-2 receptor. Hence, we conclude that specificity of Stat activation rests on coupling of the latent transcription factor to the intracellular domain of its cognate receptors (Greenlund et al., 1994; Hou et al., 1994).

Having established a molecular link between Stat 5 and the DNA binding activity induced by IL-2 in YT cells (designated Y2), we set out to determine the identity of the DNA binding activity induced by IL-2 in PBLs. Whereas the activity induced by IL-2 in both resting and PHA-stimulated PBLs (designated P2) co-migrated on non-denaturing gels with that induced in YT cells (Y2), we did not have antibodies that would allow rigorous testing of the identity of the Stat protein induced in PBLs. As such, we purified the activity in order to obtain partial amino acid sequence of the relevant polypeptides.

Lymphocytes were isolated from 10 units of human blood and grown for three days in the presence of PHA. The cells were then washed, cultured for 12 hours in the absence of PHA, exposed for 15 minutes to 10 ng/ml IL-2, harvested and used to prepare nuclear extracts. The IL-2 induced DNA binding activity was purified by the same method used to isolate Stat proteins from YT cells (Experimental Procedures).

These procedures led to the purification of two polypeptides that migrated with apparent molecular masses of 96 and 95 Kd. Western blot assays provided evidence that both of these polypeptides reacted strongly with antibodies to phosphotyrosine. Each polypeptide was excised, digested with lysine-C and the resulting peptide fragments were fractionated by capillary HPLC. The two proteins yielded very similar lysine-C digests as assessed by the UV spectral traces of the resulting chromatograms. Mass spectrometry analysis of individual, co-eluting peptides provided additional evidence of a close relatedness between the 96 and 95 Kd polypeptides. Two peptides were subjected to gas phase sequencing, yielding sequences highly related to MGF/Stat 5. We thus conclude that the predominant Stat protein induced by IL-2 in PHA-stimulated human lymphocytes is highly related to MGF/Stat 5.

A cDNA clone corresponding to the human form of Stat 5 was isolated and sequenced. Conceptual translation of the DNA sequence specified an open reading frame (ORF) of 794 amino acid residues which, in an unmodified state, predicts a molecular mass of 90,544 daltons. Segments identical to all three of the peptides derived from the IL-2 induced protein from YT cells (Y2) and one of the peptides derived from the IL-2 induced protein from PBLs (P2) were observed in the ORF. The second peptide sequence derived from the IL-2 induced protein purified from PBLs matched the ORF at five consecutive residues, yet diverged significantly at amino acid residue 687. This may represent the result of alternative splicing or presence of a second, highly related hStat 5 gene.

A comparison of the sequence of the cloned gene product, hereby designated human Stat 5 (hStat 5), and the previously characterized MGF protein of sheep (Wakao et al., 1994) reveals that although significant segments of amino acid sequence identity occur throughout the two proteins, three divergent regions are also observed (residues 90–107, 260–272 and 717-COOH). As such, the sheep and human proteins may be encoded by non-homologous genes.

The tissue distribution of hStat 5 gene expression was examined by Northern blotting. Messenger RNAs of measuring roughly 3, 4 and 6 Kb in length were observed. The larger two mRNAs were observed in all human tissues that were examined, with roughly equivalent levels occurring in placenta, skeletal muscle, spleen, thymus, prostate, testis, ovary, small intestine, colon and PBLs, slightly lower levels in heart, lung, kidney and pancreas, and considerably lover levels in brain and liver. The small (3 Kb) mRNA was observed in a more restricted pattern, limited to placenta, skeletal muscle and testis. It is unclear whether these various hStat 5 mRNAs are expressed as differentially processed products of a single gene or the transcribed products of distinct genes.

Experimental Procedures:
Cell Culture:

The transformed human lymphocyte cell line YT (Yodoi et al., 1985) was grown in RPMI-1640 culture medium supplemented with 10% fetal bovine serum, 10 mM HEPES pH 7.2, 10 mM b-mercaptoethanol, 2 mM L-glutamine, 100 mg/ml streptomycin and 100 mg/ml ampicillin. Cells grown to a density of $7 \times 10^5$/ml in T-150 flasks were exposed to recombinant IL-2 (Biosource International) for 15 minutes at 37° C., harvested by centrifugation and used to prepare nuclear extracts (Digham et al., 1983). Peripheral blood lymphocytes (PBLs) obtained from Irvin Memorial Blood Bank (San Francisco) were harvested by centrifugation, resuspended in phosphate buffered saline and applied atop Lymphoprep (Nycomed AS) in 50 ml conical centrifuge tubes. Following centrifugation the lymphocyte layer was retrieved, washed and resuspended in the same culture medium used for growth of YT cells. Cells were grown either in the presence or absence of *Phaseolus vulgaris* lectin (PHA) (Sigma) for three days. PHA stimulated cells were washed, resuspended in culture medium lacking PHA and grown for 12 hours. IL-2 treatment and preparation of nuclear extracts was the same as used for YT cells.

Purification of IL-2 induced transcription factors:

Nuclear extracts from YT cells (1 g) and PBLs (0.25 g) were precipitated with 30% ammonium sulfate. The proteins were then removed by centrifugation and the supernatant was then treated with 60% ammonium sulfate. Proteins precipitating between 30–60% ammonium sulfate were recovered by centrifugation, resuspended in 20 mM Hepes (pH 7.9), 25% (V/V) glycerol, 0.1M NACl, 1.5 mM $MgCl_2$, 0.2 mM EDTA, 0.5 mM phenylmethylsulfonate, 0.5 mM dithiothreitol (DTT), aprotinin at 1 mg/ml, pepstatin at 1 mg/ml, leupeptin at 1 mg/ml, 1 mM benzamidine, 1 mM sodium vanadate, 1 mM NaF, 5 mM b-glycerolphosphate (buffer C), and dialyzed against buffer C supplemented with NaCl to a final concentration of 150 mM.

After dialysis, insoluble proteins were removed by centrifugation and the remaining material was chromatographed over a 100 ml S-Sepharose (Pharmacia) column. Protein flow-through was mixed with a DNA-affinity resin prepared by coupling synthetic, biotinylated DNA corresponding to the IL-4 response element of the gene encoding FcgRI (5'-GTATTTCCCAGAAAAGGAAC-3) (SEQ ID NO:3) to streptavidin agarose (Sigma). After binding (2 hours at 4° C.), the affinity matrix was placed on a disposable column and washed sequentially with 10 ml of buffer C, 4 ml of buffer C supplemented with a mutated variant of the IL-4 response element (5'-GTAT<u>C</u>ACCAGT<u>C</u>AAGGAAC-3') (SEQ ID NO:4) at 0.2 mg/ml, and 10 ml of buffer C. Protein was eluted by exposure to buffer C supplemented with 0.35M NaCl, dialyzed against buffer C, and placed on a 0.5 ml Q-Sepharose (Pharmacia) column. The column was washed with 5 ml of buffer C and protein was eluted with 1 ml of buffer C supplemented with 0.35M NaCl.

Partial amino acid sequencing of IL-2 induced transcription factors:

Purified IL-2 induced DNA binding proteins were subjected to SDS-gel electrophoresis and transferred to a polyvinylidene difluoride membrane (Millipore). The membrane was stained with Coomassie blue R-250 in 40% methanol and 0.1% acetic acid for 30 seconds then destained for 5 minutes with 10% acetic acid in 50% methanol. Relevant polypeptides were excised from the membrane and alkylated with isopropylacetamide (Krutsch and Inman, 1993; Henzel et al., 1994) and then digested in 50 ul of 0.1M ammonium bicarbonate, 10% acetonitrile with 0.2 mg of lysine-C (Wako) at 37° C. for 17 hours. The solution was then concentrated to 20 ul and directly injected onto a capillary high-performance liquid chromatogram. The HPLC consisted of a prototype capillary gradient HPLC system (Waters Associates) and a model 783 UV detector equipped with a Z-shaped flow cell (LC Packings, Inc.). A 30 cm length of 0.025 mm ID glass capillary was connected to the outlet of the Z-shaped cell inside the detector housing to minimize the delay volume. The total delay volume was 0.45 ml which corresponded to a delay of 6 seconds for a flow rate of 3.5 ml/min. The short delay greatly facilitated hand collection of individual peptide peaks. Peptides were separated on a C18 capillary column (0.32 by 100 mM) (LC Packing) developed with 0.1% aqueous trifloracetic acid as buffer A and acetonitrile containing 0.07% trifluoroacetic acid as buffer B. Isolated peptides were sequenced on a 470A Applied Biosystems sequencer. Residual peptides retained on the PVDF membrane were also subjected to gas phase sequencing. In the case of hStat 5 purified from PHA stimulated PBLs, this provided partial amino acid sequence of a very large lysine-C peptide, designated PBL-MB (membrane bound) co-linear with the carboxyl terminus of the intact hStat 5 protein. The same sequence was found for this peptide regardless of whether derived from the 96 or 95 Kd polypeptides (see FIG. 5). Sequence interpretation was performed on a DEC 5900 computer (Henzel et al., 1987).

Immunodepletion, supershifting and oligonucleotide competition assays:

Protein:DNA complexes were visualized by a gel mobility shift assay under non-denaturing conditions. Specificity of protein:DNA interaction was tested using 100-fold molar excess of either the native FcgRI probe (5'-GTATTTCCCAGAAAAGGAAC-3', SEQ ID NO: 3) or the mutated derivative (5'-GTAT<u>C</u>ACCCAGT<u>C</u>AAGGAAC-3', SEQ ID NO: 4). Antibody supershift experiments were performed by incubating protein samples with antibodies (Santa Cruz Biotech) for 30 minutes at 4° C. prior to exposure to the FcgRI DNA probe. Proteins purified from YT cells were purged of Stat 1 and Stat 3 by immunodepletion. 500 mg of each antibody (specific to Stat 1 and Stat 3) were incubated for 2 hours at room temperature with a slurry of protein-A Sepharose beads (Pharmacia) sufficient to yield 100 ml of bed volumn. Beads were washed three times with 1 ml of buffer C and then incubated for 2 hours at room temperature with Stat proteins purified from IL-2 induced YT cells. Beads were recovered by centrifugation and washed three times with 1 ml of buffer C. Unbound, wash and bound fractions were recovered and subjected to SDS-gel electrophoresis for subsequent staining with Coomassie blue, anti-phosphotyrosine antibodies and Stat antibodies.

Mass spectrometry:

Aliquots (0.2 ml) of the capillary HPLC purified lysine-C peptides were mixed on the sample probe tip with 0.2 ml of a-cyano-4-hydroxycinnamic acid (saturated in 50% acitonitrile 2% TFA). MALDI mass spectra were obtained with a Vestec (Houston, Tex.) LaserTec Research laser desorption linear time-of-flash mass spectrometer equipped with a 337 nm VSL-337 ND nitrogen laser (Laser Sciences, Inc).

Cloning of hStat 5 cDNA:

A cDNA library prepared from human umbilical vein endothelial cells was probed at low stringency with a fragment of the IL-4 Stat cDNA (Hou et al., 1994) corresponding to the SH3 and SH2 domains of the protein. Radiolabeled probe DNA was hybridized with filter lifts at 42° C. in a solution containing 20% formamide, 10× Denhards, 5× SSPE, 0.5% SDS and 100 mg/ml salmon sperm DNA. After hybridization (16 hours) filters were washed twice at 42° C. in a 2× SSPE, 0.5% SDS and twice at 42° C. in 2× SSPE. Roughly equivalent numbers of clones encoding IL-4 Stat and hStat 5 were recovered. A 3.8 Kb hStat 5 cDNA clone was sequenced on both DNA strands using an Applied Biosystems automated DNA sequencer.

Northern Blotting:

RNA blot hybridization with a uniformly labeled DNA probe prepared from the hStat 5 cDNA clone and Multiple Tissue Northern Blot membranes (Clone-tech) were used. The probe DNA fragment corresponded to the region of the hStat 5 cDNA that encodes the amino terminal segment of the protein (excluding the putative SH3 and SH2 domains). Probe labeling, hybridization and membrane washing were performed as described (Sambrook et al., 1989).

Cited References:

Aebersold et al., (1991) *Anal. Biochem.* 199:51–60; Akira et al., (1994) *Cell* 77:63–71; Beadling et al., (1994) *EMBO J.* 13:5605–5615; Boussiotis et al., (1994) *Science* 266:1039–1042; Darnell et al., (1994) *Science* 264:1415–1421; Dignam et al., (1983) *Nucl. Acids Res.* 11:1475–99; Cosman et al., (1984) *Nature* 312:768–771; Gilmore et al., (1994) *Proc. Natl. Acad. Sci. U.S.A.* 91:6850–6854; Giri et al., (1994) *EMBO J.* 13:2822–2830; Gouilleux et al., (1994) *EMBO J.* 13:4361–4369; Greenlund et al., (1994) *The EMBO J.* 13:1591–1600; Hatakeyama et al., (1989) *Science* 244:551–556; Henzel et al., (1994) *Methods: Companion Methods Enzymol.* 6:239–247; Henzel et al., (1987) *J. Chromatogr.* 404:41–52; Hou et al., (1994) *Science* 265:1701–1706; Kawahara et al., (1994) Mol. Cell. Biol. 14:5433–5440; Kelly et al., (1991) *Endocrine Rev.* 12:235–251; Kondo et al., (1993) *Science* 262:1874–1877; Kotanides et al., (1993) *Science* 262: 1265–1267; Krutzsch et al., (1993) *Anal. Biochem.* 209:109–116; Leonard et al., (1984) *Nature* 311:626–631; Minamoro et al., (1990) *J. Immunol.* 145:217–2182; Miyazaki et al., (1994) *Science*

266:1045–1047; Nakamura et al., (1994) *Nature* 369:330–333; Nelson et al., (1994) *Nature* 369:333–336; Nikaido et al., (1984) *Nature* 311:631–635; Noguchi et al., (1993) *Science* 262:1877–1880; Rui et al., (1994) *J. Biol. Chem.* 269:5364–5368; Russell et al., (1994) *Science* 266:1042–1045; Sambrook et al., (1989) Molecular Cloning (Cold Spring Harbor: Cold Spring Harbor Laboratory); Schindler et al., (1992) *Proc. Natl. Acad. Sci. U.S.A.* 89:7836–7839; Smith (1988) *Science* 240:1169–1176; Takeshita et al., (1992) *Science* 257:379–382; Takeshita et al., (1990) *Int. Immunol.* 2:477–480; Taniguchi et al., (1986) *Immunol. Rev.* 92:121–133; Taniguchi and Minami (1993) *Cell* 73:5–8; Voss et al., (1993) *Proc. Natl. Acad. Sci. U.S.A.* 90:2428–2432; Waldmann (1993) *Immunol. Today* 15:19–26; Wakao et al., (1994) *The EMBO J.* 13:2182–2191; Yip and Hutchens (1992) *FEBS Lett.* 308:149–153; and Yodoi et al., (1985) *J. Immun.* 134:1623–1630.

EXAMPLES

1. Protocol for hStat 5-IL-2 Receptor-peptide binding assay.
   A. Reagents:
   Neutralite Avidin: 20 μg/ml in PBS.
   Blocking buffer: 5% BSA, 0.5% Tween 20 in PBS; 1 hr, RT.
   Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
   $^{33}$P hStat 5 10× stock: $10^{-8}$–$10^{-6}$M "cold" hStat 5 supplemented with 200,000–250,000 cpm of labeled, inactive and truncated hStat 5 (Beckman counter). Place in the 4° C. microfridge during screening.
   Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
   IL-2-receptor-peptides: $10^{-8}$–$10^{-5}$M of each IL-2 receptor biotinylated peptides in PBS.
   B. Preparation of assay plates:
   Coat with 120 μl of stock N-Avidin per well overnight at 4° C.
   Wash 2× with 200 μl PBS.
   Block with 150 μl of blocking buffer.
   Wash 2× with 200 μl PBS.
   C. Assay:
   Add 40 μl assay buffer/well.
   Add 10 μl compound or extract.
   Add 10 μl $^{33}$P-hStat 5 (20,000–25,000 cpm/0.1–10 pmoles/well=$10^{-9}$–$10^{-7}$M final concentration).
   Shake at 25 C. for 15 min.
   Incubate additional 45 min. at 25 C.
   Add 40 μl IL-2 receptor peptide mixture (0.1–10 pmoles/40 ul in assay buffer)
   Incubate 1 hr at RT.
   Stop the reaction by washing 4× with 200 μl PBS.
   Add 150 μl scintillation cocktail.
   Count in Topcount.
   D. Controls for all assays (located on each plate):
   a. Non-specific binding (no receptor peptide added)
   b. Soluble (non-biotinylated receptor peptide) at 80% inhibition.

2. Protocol for hStat 5-DNA binding assay.
   A. Reagents:
   Neutralite Avidin: 20 ug/ml in PBS.
   Blocking buffer: 5% BSA, 0.5% Tween 20 in PBS; 1 hr, RT.
   Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
   $^{33}$P hStat 5 10× stock: $10^{-6}$–$10^{-8}$M "cold" hStat 5 supplemented with 200,000–250,000 cpm of labeled hStat 5 (Beckman counter). Place in the 4° C. microfridge during screening.
   Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
   Oligonucleotide stock: (specific biotinylated). Biotinylated oligo at 17 pmole/μl, hStat 5 binding site: (BIOTIN)-GTATTTCCCAGAAAAGGAAC (SEQ ID NO: 3)
   B. Preparation of assay plates:
   Coat with 120 μl of stock N-Avidin per well overnight at 4° C.
   Wash 2× with 200 μl PBS.
   Block with 150 μl of blocking buffer.
   Wash 2× with 200 μl PBS.
   C. Assay:
   Add 40 μl assay buffer/well.
   Add 10 μl compound or extract.
   Add 10 μl $^{33}$P-hStat 5 (20,000–25,000 cpm/0.1–10 pmoles/well=$10^{-9}$–$10^{-7}$M final concentration).
   Shake at 25 C. for 15 min.
   Incubate additional 45 min. at 25 C.
   Add 40 μl oligo mixture (1.0 pmoles/40 ul in assay buffer with 1 ng of ss-DNA)
   Incubate 1 hr at RT.
   Stop the reaction by washing 4× with 200 μl PBS.
   Add 150 μl scintillation cocktail.
   Count in Topcount.
   D. Controls for all assays (located on each plate):
   a. Non-specific binding (no oligo added)
   b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid encoding a human Signal Transducer and Activator of Transcription number 5, hSTAT5 (SEQ ID NO:2) or an hSTAT5 peptide comprising at least one amino acid sequence selected from the group consisting of ATQLQK (SEQ ID NO:2, residues 91–96), YDRCPLELV (SEQ ID NO:2, residues 98–106), NNCSSP (SEQ ID NO:2, residues 124–129), QQLAGNGG (SEQ ID NO:2, residues 259–266), NGGPPEG (SEQ ID NO:2, residues 264–270), NASADAG (SEQ ID NO:2, residues 708–714), SPAVCPQAP (SEQ ID NO:2, residues 726–734), HVLDQDGEF (SEQ ID NO:2, residues 744–752), MDSLDSRLS (SEQ ID NO:2, residues 772–780), and FTSARGSLS (SEQ ID NO:2, residues 786–794).

2. The isolated nucleic acid according to claim 1, wherein said nucleic acid encodes hSTAT5 (SEQ ID NO:2).

3. The isolated nucleic acid according to claim 1, wherein said nucleic acid comprises SEQ ID NO:1.

4. The isolated nucleic acid according to claim 1, wherein said nucleic acid encodes an hSTAT5 peptide comprising amino acid sequence ATQLQK (SEQ ID NO:2, residues 91–96).

5. The isolated nucleic acid according to claim 1, wherein said nucleic acid encodes an hSTAT5 peptide comprising amino acid sequence YDRCPLELV (SEQ ID NO:2, residues 98–106).

6. The isolated nucleic acid according to claim 1, wherein said nucleic acid encodes an hSTAT5 peptide comprising amino acid sequence NNCSSP (SEQ ID NO:2, residues 124–129).

7. The isolated nucleic acid according to claim 1, wherein said nucleic acid encodes an hSTAT5 peptide comprising amino acid sequence QQLAGNGG (SEQ ID NO:2, residues 259–266).

8. The isolated nucleic acid according to claim 1, wherein said nucleic acid encodes an hSTAT5 peptide comprising amino acid sequence NGGPPEG (SEQ ID NO:2, residues 264–270).

9. The isolated nucleic acid according to claim 1, wherein said nucleic acid encodes an hSTAT5 peptide comprising amino acid sequence NASADAG (SEQ ID NO:2, residues 708–714).

10. The isolated nucleic acid according to claim 1, wherein said nucleic acid encodes an hSTAT5 peptide comprising amino acid sequence SPAVCPQAP (SEQ ID NO:2, residues 726–734).

11. The isolated nucleic acid according to claim 1, wherein said nucleic acid encodes an hSTAT5 peptide comprising amino acid sequence HVLDQDGEF (SEQ ID NO:2, residues 744–752).

12. The isolated nucleic acid according to claim 1, wherein said nucleic acid encodes an hSTAT5 peptide comprising amino acid sequence MDSLDSRLS (SEQ ID NO:2, residues 772–780).

13. The isolated nucleic acid according to claim 1, wherein said nucleic acid encodes an hSTAT5 peptide comprising amino acid sequence FTSARGSLS (SEQ ID NO:2, residues 786–794).

14. A vector comprising a nucleic acid having an open reading frame encoding hSTAT5 (SEQ ID NO:2) or an hSTAT5 peptide comprising at least one amino acid sequence selected from the group consisting of ATQLQK (SEQ ID NO:2, residues 91–96), YDRCPLELV (SEQ ID NO:2, residues 98–106), NNCSSP (SEQ ID NO:2, residues 124–129), QQLAGNGG (SEQ ID NO:2, residues 259–266), NGGPPEG (SEQ ID NO:2, residues 264–270), NASADAG (SEQ ID NO:2, residues 708–714), SPAVCPQAP (SEQ ID NO:2, residues 726–734), HVLDQDGEF (SEQ ID NO:2, residues 744–752), MDSLDSRLS (SEQ ID NO:2, residues 772–780), and FTSARGSLS (SEQ ID NO:2, residues 786–794), said open reading frame joined in sequence directly to a nucleotide sequence not naturally joined to said open reading frame.

15. The vector according to claim 14, wherein said nucleic acid encodes hSTAT5 (SEQ ID NO:2).

16. The vector according to claim 14, wherein said nucleic acid comprises SEQ ID NO:1.

17. The vector according to claim 14, wherein said open reading frame is operably linked to a transcription regulatory element.

18. The vector according to claim 15, wherein said open reading frame is operably linked to a transcription regulatory element.

19. The vector according to claim 16, wherein said open reading frame is operably linked to a transcription regulatory element.

20. An isolated cell comprising a nucleic acid having an open reading frame encoding hSTAT5 (SEQ ID NO:2) or an hSTAT5 peptide comprising at least one amino acid sequence selected from the group consisting of ATQLQK (SEQ ID NO:2, residues 91–96), YDRCPLELV (SEQ ID NO:2, residues 98–106), NNCSSP (SEQ ID NO:2, residues 124–129), QQLAGNGG (SEQ ID NO:2, residues 259–266), NGGPPEG (SEQ ID NO:2, residues 264–270), NASADAG (SEQ ID NO:2, residues 708–714), SPAVCPQAP (SEQ ID NO:2, residues 726–734), HVLDQDGEF (SEQ ID NO:2, residues 744–752), MDSLDSRLS (SEQ ID NO:2, residues 772–780), and FTSARGSLS (SEQ ID NO:2, residues 786–794), said open reading frame joined in sequence directly to a nucleotide sequence not naturally joined to said open reading frame.

21. The cell according to claim 20, wherein said open reading frame encodes hSTAT5 (SEQ ID NO:2).

22. The cell according to claim 20, wherein said open reading frame comprises SEQ ID NO:1.

23. The cell according to claim 20, wherein said open reading frame is operably linked to a transcription regulatory element.

24. The cell according to claim 21, wherein said open reading frame is operably linked to a transcription regulatory element.

25. The cell according to claim 22, wherein said open reading frame is operably linked to a transcription regulatory element.

26. A method of making recombinant hSTAT5 (SEQ ID NO:2) or an hSTAT5 peptide, said method comprising culturing the cell according to claim 23 and recovering said recombinant hSTAT5 or said hSTAT5 peptide.

27. A method of making recombinant hSTAT5 (SEQ ID NO:2) or an hSTAT5 peptide, said method comprising culturing the cell according to claim 24 and recovering said recombinant hSTAT5 or said hSTAT5 peptide.

28. A method of making recombinant hSTAT5 (SEQ ID NO:2) or an hSTAT5 peptide, said method comprising culturing the cell according to claim 25 and recovering said recombinant hSTAT5 or said hSTAT5 peptide.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 2385 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..2382

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GCG | GGC | TGG | ATC | CAG | GCC | CAG | CAG | CTG | CAG | GGA | GAC | GCG | CTG | CGC | 48 |
| Met | Ala | Gly | Trp | Ile | Gln | Ala | Gln | Gln | Leu | Gln | Gly | Asp | Ala | Leu | Arg | |
| 1 | | | | 5 | | | | | 10 | | | | | 15 | | |
| CAG | ATG | CAG | GTG | CTG | TAC | GGC | CAG | CAC | TTC | CCC | ATC | GAG | GTC | CGG | CAC | 96 |
| Gln | Met | Gln | Val | Leu | Tyr | Gly | Gln | His | Phe | Pro | Ile | Glu | Val | Arg | His | |
| | | | 20 | | | | | 25 | | | | | 30 | | | |
| TAC | TTG | GCC | CAG | TGG | ATT | GAG | AGC | CAG | CCA | TGG | GAT | GCC | ATT | GAC | TTG | 144 |
| Tyr | Leu | Ala | Gln | Trp | Ile | Glu | Ser | Gln | Pro | Trp | Asp | Ala | Ile | Asp | Leu | |
| | | 35 | | | | | 40 | | | | | 45 | | | | |
| GAC | AAT | CCC | CAG | GAC | AGA | GCC | CAA | GCC | ACC | CAG | CTC | CTG | GAG | GGC | CTG | 192 |
| Asp | Asn | Pro | Gln | Asp | Arg | Ala | Gln | Ala | Thr | Gln | Leu | Leu | Glu | Gly | Leu | |
| | 50 | | | | | 55 | | | | | 60 | | | | | |
| GTG | CAG | GAG | CTG | CAG | AAG | AAG | GCG | GAG | CAC | CAG | GTG | GGG | GAA | GAT | GGG | 240 |
| Val | Gln | Glu | Leu | Gln | Lys | Lys | Ala | Glu | His | Gln | Val | Gly | Glu | Asp | Gly | |
| 65 | | | | | 70 | | | | | 75 | | | | | 80 | |
| TTT | TTA | CTG | AAG | ATC | AAG | CTG | GGG | CAC | TAC | GCC | ACG | CAG | CTC | CAG | AAA | 288 |
| Phe | Leu | Leu | Lys | Ile | Lys | Leu | Gly | His | Tyr | Ala | Thr | Gln | Leu | Gln | Lys | |
| | | | | 85 | | | | | 90 | | | | | 95 | | |
| ACA | TAT | GAC | CGC | TGC | CCC | CTG | GAG | CTG | GTC | CGC | TGC | ATC | CGG | CAC | ATT | 336 |
| Thr | Tyr | Asp | Arg | Cys | Pro | Leu | Glu | Leu | Val | Arg | Cys | Ile | Arg | His | Ile | |
| | | | 100 | | | | | 105 | | | | | 110 | | | |
| CTG | TAC | AAT | GAA | CAG | AGG | CTG | GTC | CGA | GAA | GCC | AAC | AAT | TGC | AGC | TCT | 384 |
| Leu | Tyr | Asn | Glu | Gln | Arg | Leu | Val | Arg | Glu | Ala | Asn | Asn | Cys | Ser | Ser | |
| | | 115 | | | | | 120 | | | | | 125 | | | | |
| CCG | GCT | GGG | ATC | CTG | GTT | GAC | GCC | ATG | TCC | CAG | AAG | CAC | CTT | CAG | ATC | 432 |
| Pro | Ala | Gly | Ile | Leu | Val | Asp | Ala | Met | Ser | Gln | Lys | His | Leu | Gln | Ile | |
| | 130 | | | | | 135 | | | | | 140 | | | | | |
| AAC | CAG | ACA | TTT | GAG | GAG | CTG | CGA | CTG | GTC | ACG | CAG | GAC | ACA | GAG | AAT | 480 |
| Asn | Gln | Thr | Phe | Glu | Glu | Leu | Arg | Leu | Val | Thr | Gln | Asp | Thr | Glu | Asn | |
| 145 | | | | | 150 | | | | | 155 | | | | | 160 | |
| GAG | CTG | AAG | AAA | CTG | CAG | CAG | ACT | CAG | GAG | TAC | TTC | ATC | ATC | CAG | TAC | 528 |
| Glu | Leu | Lys | Lys | Leu | Gln | Gln | Thr | Gln | Glu | Tyr | Phe | Ile | Ile | Gln | Tyr | |
| | | | | 165 | | | | | 170 | | | | | 175 | | |
| CAG | GAG | AGC | CTG | AGG | ATC | CAA | GCT | CAG | TTT | GCC | CAG | CTG | GCC | CAG | CTG | 576 |
| Gln | Glu | Ser | Leu | Arg | Ile | Gln | Ala | Gln | Phe | Ala | Gln | Leu | Ala | Gln | Leu | |
| | | | 180 | | | | | 185 | | | | | 190 | | | |
| AGC | CCC | CAG | GAG | CGT | CTG | AGC | CGG | GAG | ACG | GCC | CTC | CAG | CAG | AAG | CAG | 624 |
| Ser | Pro | Gln | Glu | Arg | Leu | Ser | Arg | Glu | Thr | Ala | Leu | Gln | Gln | Lys | Gln | |
| | | 195 | | | | | 200 | | | | | 205 | | | | |
| GTG | TCT | CTG | GAG | GCC | TGG | TTG | CAG | CGT | GAG | GCA | CAG | ACA | CTG | CAG | CAG | 672 |
| Val | Ser | Leu | Glu | Ala | Trp | Leu | Gln | Arg | Glu | Ala | Gln | Thr | Leu | Gln | Gln | |
| | 210 | | | | | 215 | | | | | 220 | | | | | |

| | | | | | | | | | | | | | | | | |
|---|---|---|---|---|---|---|---|---|---|---|---|---|---|---|---|---|
| TAC | CGC | GTG | GAG | CTG | GCC | GAG | AAG | CAC | CAG | AAG | ACC | CTG | CAG | CTG | CTG | 720 |
| Tyr | Arg | Val | Glu | Leu | Ala | Glu | Lys | His | Gln | Lys | Thr | Leu | Gln | Leu | Leu | |
| 225 | | | | 230 | | | | | 235 | | | | | 240 | | |
| CGG | AAG | CAG | CAG | ACC | ATC | ATC | CTG | GAT | GAC | GAG | CTG | ATC | CAG | TGG | AAG | 768 |
| Arg | Lys | Gln | Gln | Thr | Ile | Ile | Leu | Asp | Asp | Glu | Leu | Ile | Gln | Trp | Lys | |
| | | | | 245 | | | | | 250 | | | | | 255 | | |
| CGG | CGG | CAG | CAG | CTG | GCC | GGG | AAC | GGC | GGG | CCC | CCC | GAG | GGC | AGC | CTG | 816 |
| Arg | Arg | Gln | Gln | Leu | Ala | Gly | Asn | Gly | Gly | Pro | Pro | Glu | Gly | Ser | Leu | |
| | | | 260 | | | | | 265 | | | | | 270 | | | |
| GAC | GTG | CTA | CAG | TCC | TGG | TGT | GAG | AAG | TTG | GCC | GAG | ATC | ATC | TGG | CAG | 864 |
| Asp | Val | Leu | Gln | Ser | Trp | Cys | Glu | Lys | Leu | Ala | Glu | Ile | Ile | Trp | Gln | |
| | | 275 | | | | | 280 | | | | | 285 | | | | |
| AAC | CGG | CAG | CAG | ATC | CGC | AGG | GCT | GAG | CAC | CTC | TGC | CAG | CAG | CTG | CCC | 912 |
| Asn | Arg | Gln | Gln | Ile | Arg | Arg | Ala | Glu | His | Leu | Cys | Gln | Gln | Leu | Pro | |
| | 290 | | | | | 295 | | | | | 300 | | | | | |
| ATC | CCC | GGC | CCA | GTG | GAG | GAG | ATG | CTG | GCC | GAG | GTC | AAC | GCC | ACC | ATC | 960 |
| Ile | Pro | Gly | Pro | Val | Glu | Glu | Met | Leu | Ala | Glu | Val | Asn | Ala | Thr | Ile | |
| 305 | | | | | 310 | | | | | 315 | | | | | 320 | |
| ACG | GAC | ATT | ATC | TCA | GCC | CTG | GTG | ACC | AGC | ACA | TTC | ATC | ATT | GAG | AAG | 1008 |
| Thr | Asp | Ile | Ile | Ser | Ala | Leu | Val | Thr | Ser | Thr | Phe | Ile | Ile | Glu | Lys | |
| | | | | 325 | | | | | 330 | | | | | 335 | | |
| CAG | CCT | CCT | CAG | GTC | CTG | AAG | ACC | CAG | ACC | AAG | TTT | GCA | GCC | ACC | GTA | 1056 |
| Gln | Pro | Pro | Gln | Val | Leu | Lys | Thr | Gln | Thr | Lys | Phe | Ala | Ala | Thr | Val | |
| | | | 340 | | | | | 345 | | | | | 350 | | | |
| CGC | CTG | CTG | GTG | GGC | GGG | AAG | CTG | AAC | GTG | CAC | ATG | AAT | CCC | CCC | CAG | 1104 |
| Arg | Leu | Leu | Val | Gly | Gly | Lys | Leu | Asn | Val | His | Met | Asn | Pro | Pro | Gln | |
| | | 355 | | | | | 360 | | | | | 365 | | | | |
| GTG | AAG | GCC | ACC | ATC | ATC | AGT | GAG | CAG | CAG | GCC | AAG | TCT | CTG | CTT | AAA | 1152 |
| Val | Lys | Ala | Thr | Ile | Ile | Ser | Glu | Gln | Gln | Ala | Lys | Ser | Leu | Leu | Lys | |
| | 370 | | | | | 375 | | | | | 380 | | | | | |
| AAT | GAG | AAC | ACC | CGC | AAC | GAG | TGC | AGT | GGT | GAG | ATC | CTG | AAC | AAC | TGC | 1200 |
| Asn | Glu | Asn | Thr | Arg | Asn | Glu | Cys | Ser | Gly | Glu | Ile | Leu | Asn | Asn | Cys | |
| 385 | | | | | 390 | | | | | 395 | | | | | 400 | |
| TGC | GTG | ATG | GAG | TAC | CAC | CAA | GCC | ACG | GGC | ACC | CTC | AGT | GCC | CAC | TTC | 1248 |
| Cys | Val | Met | Glu | Tyr | His | Gln | Ala | Thr | Gly | Thr | Leu | Ser | Ala | His | Phe | |
| | | | | 405 | | | | | 410 | | | | | 415 | | |
| AGG | AAC | ATG | TCA | CTG | AAG | AGG | ATC | AAG | CGT | GCT | GAC | CGG | CGG | GGT | GCA | 1296 |
| Arg | Asn | Met | Ser | Leu | Lys | Arg | Ile | Lys | Arg | Ala | Asp | Arg | Arg | Gly | Ala | |
| | | | 420 | | | | | 425 | | | | | 430 | | | |
| GAG | TCC | GTG | ACA | GAG | GAG | AAG | TTC | ACA | GTC | CTG | TTT | GAG | TCT | CAG | TTC | 1344 |
| Glu | Ser | Val | Thr | Glu | Glu | Lys | Phe | Thr | Val | Leu | Phe | Glu | Ser | Gln | Phe | |
| | | 435 | | | | | 440 | | | | | 445 | | | | |
| AGT | GTT | GGC | AGC | AAT | GAG | CTT | GTG | TTC | CAG | GTG | AAG | ACT | CTG | TCC | CTA | 1392 |
| Ser | Val | Gly | Ser | Asn | Glu | Leu | Val | Phe | Gln | Val | Lys | Thr | Leu | Ser | Leu | |
| | 450 | | | | | 455 | | | | | 460 | | | | | |
| CCT | GTG | GTT | GTC | ATC | GTC | CAC | GGC | AGC | CAG | GAC | CAC | AAT | GCC | ACG | GCT | 1440 |
| Pro | Val | Val | Val | Ile | Val | His | Gly | Ser | Gln | Asp | His | Asn | Ala | Thr | Ala | |
| 465 | | | | | 470 | | | | | 475 | | | | | 480 | |
| ACT | GTG | CTG | TGG | GAC | AAT | GCC | TTT | GCT | GAG | CCG | GGC | AGG | GTG | CCA | TTT | 1488 |
| Thr | Val | Leu | Trp | Asp | Asn | Ala | Phe | Ala | Glu | Pro | Gly | Arg | Val | Pro | Phe | |
| | | | | 485 | | | | | 490 | | | | | 495 | | |
| GCC | GTG | CCT | GAC | AAA | GTG | CTG | TGG | CCG | CAG | CTG | TGT | GAG | GCG | CTC | AAC | 1536 |
| Ala | Val | Pro | Asp | Lys | Val | Leu | Trp | Pro | Gln | Leu | Cys | Glu | Ala | Leu | Asn | |
| | | | 500 | | | | | 505 | | | | | 510 | | | |
| ATG | AAA | TTC | AAG | GCC | GAA | GTG | CAG | AGC | AAC | CGG | GGC | CTG | ACC | AAG | GAG | 1584 |
| Met | Lys | Phe | Lys | Ala | Glu | Val | Gln | Ser | Asn | Arg | Gly | Leu | Thr | Lys | Glu | |
| | | 515 | | | | | 520 | | | | | 525 | | | | |
| AAC | CTC | GTG | TTC | CTG | GCG | CAG | AAA | CTG | TTC | AAC | AAC | AGC | AGC | AGC | CAC | 1632 |
| Asn | Leu | Val | Phe | Leu | Ala | Gln | Lys | Leu | Phe | Asn | Asn | Ser | Ser | Ser | His | |
| | 530 | | | | | 535 | | | | | 540 | | | | | |

| | | | | | | | | | | | | | | | | |
|---|---|---|---|---|---|---|---|---|---|---|---|---|---|---|---|---|
| CTG | GAG | GAC | TAC | AGT | GGC | CTG | TCC | GTG | TCC | TGG | TCC | CAG | TTC | AAC | AGG | 1680 |
| Leu | Glu | Asp | Tyr | Ser | Gly | Leu | Ser | Val | Ser | Trp | Ser | Gln | Phe | Asn | Arg | |
| 545 | | | | 550 | | | | | 555 | | | | | | 560 | |
| GAG | AAC | TTG | CCG | GGC | TGG | AAC | TAC | ACC | TTC | TGG | CAG | TGG | TTT | GAC | GGG | 1728 |
| Glu | Asn | Leu | Pro | Gly | Trp | Asn | Tyr | Thr | Phe | Trp | Gln | Trp | Phe | Asp | Gly | |
| | | | | 565 | | | | | 570 | | | | | 575 | | |
| GTG | ATG | GAG | GTG | TTG | AAG | AAG | CAC | CAC | AAG | CCC | CAC | TGG | AAT | GAT | GGG | 1776 |
| Val | Met | Glu | Val | Leu | Lys | Lys | His | His | Lys | Pro | His | Trp | Asn | Asp | Gly | |
| | | | 580 | | | | | 585 | | | | | | 590 | | |
| GCC | ATC | CTA | GGT | TTT | GTG | AAT | AAG | CAA | CAG | GCC | CAC | GAC | CTG | CTC | ATC | 1824 |
| Ala | Ile | Leu | Gly | Phe | Val | Asn | Lys | Gln | Gln | Ala | His | Asp | Leu | Leu | Ile | |
| | | 595 | | | | | 600 | | | | | 605 | | | | |
| AAC | AAG | CCC | GAC | GGG | ACC | TTC | TTG | TTG | CGC | TTT | AGT | GAC | TCA | GAA | ATC | 1872 |
| Asn | Lys | Pro | Asp | Gly | Thr | Phe | Leu | Leu | Arg | Phe | Ser | Asp | Ser | Glu | Ile | |
| | 610 | | | | | 615 | | | | | 620 | | | | | |
| GGG | GGC | ATC | ACC | ATC | GCC | TGG | AAG | TTT | GAC | TCC | CCG | GAA | CGC | AAC | CTG | 1920 |
| Gly | Gly | Ile | Thr | Ile | Ala | Trp | Lys | Phe | Asp | Ser | Pro | Glu | Arg | Asn | Leu | |
| 625 | | | | | 630 | | | | | 635 | | | | | 640 | |
| TGG | AAC | CTG | AAA | CCA | TTC | ACC | ACG | CGG | GAT | TTC | TCC | ATC | AGG | TCC | CTG | 1968 |
| Trp | Asn | Leu | Lys | Pro | Phe | Thr | Thr | Arg | Asp | Phe | Ser | Ile | Arg | Ser | Leu | |
| | | | | 645 | | | | | 650 | | | | | 655 | | |
| GCT | GAC | CGG | CTG | GGG | GAC | CTG | AGC | TAT | CTC | ATC | TAT | GTG | TTT | CCT | GAC | 2016 |
| Ala | Asp | Arg | Leu | Gly | Asp | Leu | Ser | Tyr | Leu | Ile | Tyr | Val | Phe | Pro | Asp | |
| | | | 660 | | | | | 665 | | | | | 670 | | | |
| CGC | CCC | AAG | GAT | GAG | GTC | TTC | TCC | AAG | TAC | TAC | ACT | CCT | GTG | CTG | GCT | 2064 |
| Arg | Pro | Lys | Asp | Glu | Val | Phe | Ser | Lys | Tyr | Tyr | Thr | Pro | Val | Leu | Ala | |
| | | 675 | | | | | 680 | | | | | 685 | | | | |
| AAA | GCT | GTT | GAT | GGA | TAT | GTG | AAA | CCA | CAG | ATC | AAG | CAA | GTG | GTC | CCT | 2112 |
| Lys | Ala | Val | Asp | Gly | Tyr | Val | Lys | Pro | Gln | Ile | Lys | Gln | Val | Val | Pro | |
| | 690 | | | | | 695 | | | | | 700 | | | | | |
| GAG | TTT | GTG | AAT | GCA | TCT | GCA | GAT | GCT | GGG | GGC | AGC | AGC | GCC | ACG | TAC | 2160 |
| Glu | Phe | Val | Asn | Ala | Ser | Ala | Asp | Ala | Gly | Gly | Ser | Ser | Ala | Thr | Tyr | |
| 705 | | | | | 710 | | | | | 715 | | | | | 720 | |
| ATG | GAC | CAG | GCC | CCC | TCC | CCA | GCT | GTG | TGC | CCC | CAG | GCT | CCC | TAT | AAC | 2208 |
| Met | Asp | Gln | Ala | Pro | Ser | Pro | Ala | Val | Cys | Pro | Gln | Ala | Pro | Tyr | Asn | |
| | | | | 725 | | | | | 730 | | | | | 735 | | |
| ATG | TAC | CCA | CAG | AAC | CCT | GAC | CAT | GTA | CTC | GAT | CAG | GAT | GGA | GAA | TTC | 2256 |
| Met | Tyr | Pro | Gln | Asn | Pro | Asp | His | Val | Leu | Asp | Gln | Asp | Gly | Glu | Phe | |
| | | | 740 | | | | | 745 | | | | | 750 | | | |
| GAC | CTG | GAT | GAG | ACC | ATG | GAT | GTG | GCC | AGG | CAC | GTG | GAG | GAA | CTC | TTA | 2304 |
| Asp | Leu | Asp | Glu | Thr | Met | Asp | Val | Ala | Arg | His | Val | Glu | Glu | Leu | Leu | |
| | | 755 | | | | | 760 | | | | | 765 | | | | |
| CGC | CGA | CCA | ATG | GAC | AGT | CTT | GAC | TCC | CGC | CTC | TCG | CCC | CCT | GCC | GGT | 2352 |
| Arg | Arg | Pro | Met | Asp | Ser | Leu | Asp | Ser | Arg | Leu | Ser | Pro | Pro | Ala | Gly | |
| | 770 | | | | | 775 | | | | | 780 | | | | | |
| CTT | TTC | ACC | TCT | GCC | AGA | GGC | TCC | CTC | TCA | TGA | | | | | | 2385 |
| Leu | Phe | Thr | Ser | Ala | Arg | Gly | Ser | Leu | Ser | | | | | | | |
| 785 | | | | | 790 | | | | | | | | | | | |

( 2 ) INFORMATION FOR SEQ ID NO:2:

( i ) SEQUENCE CHARACTERISTICS:
        ( A ) LENGTH: 794 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Gly | Trp | Ile | Gln | Ala | Gln | Gln | Leu | Gln | Gly | Asp | Ala | Leu | Arg |
| 1 | | | | 5 | | | | | 10 | | | | | 15 | |
| Gln | Met | Gln | Val | Leu | Tyr | Gly | Gln | His | Phe | Pro | Ile | Glu | Val | Arg | His |

|    |    |    |    | 20  |    |    |    | 25  |    |    |    | 30  |    |    |
|----|----|----|----|-----|----|----|----|-----|----|----|----|-----|----|----|

Tyr Leu Ala Gln Trp Ile Glu Ser Gln Pro Trp Asp Ala Ile Asp Leu
         35                      40                 45

Asp Asn Pro Gln Asp Arg Ala Gln Ala Thr Gln Leu Leu Glu Gly Leu
         50              55                  60

Val Gln Glu Leu Gln Lys Lys Ala Glu His Gln Val Gly Glu Asp Gly
 65              70                  75                       80

Phe Leu Leu Lys Ile Lys Leu Gly His Tyr Ala Thr Gln Leu Gln Lys
                 85                  90                       95

Thr Tyr Asp Arg Cys Pro Leu Glu Leu Val Arg Cys Ile Arg His Ile
             100             105             110

Leu Tyr Asn Glu Gln Arg Leu Val Arg Glu Ala Asn Asn Cys Ser Ser
         115             120             125

Pro Ala Gly Ile Leu Val Asp Ala Met Ser Gln Lys His Leu Gln Ile
     130             135             140

Asn Gln Thr Phe Glu Glu Leu Arg Leu Val Thr Gln Asp Thr Glu Asn
145             150             155                         160

Glu Leu Lys Lys Leu Gln Gln Thr Gln Glu Tyr Phe Ile Ile Gln Tyr
             165             170             175

Gln Glu Ser Leu Arg Ile Gln Ala Gln Phe Ala Gln Leu Ala Gln Leu
             180             185             190

Ser Pro Gln Glu Arg Leu Ser Arg Glu Thr Ala Leu Gln Gln Lys Gln
         195             200             205

Val Ser Leu Glu Ala Trp Leu Gln Arg Glu Ala Gln Thr Leu Gln Gln
     210             215             220

Tyr Arg Val Glu Leu Ala Glu Lys His Gln Lys Thr Leu Gln Leu Leu
225             230             235                         240

Arg Lys Gln Gln Thr Ile Ile Leu Asp Asp Glu Leu Ile Gln Trp Lys
             245             250             255

Arg Arg Gln Gln Leu Ala Gly Asn Gly Gly Pro Pro Glu Gly Ser Leu
             260             265             270

Asp Val Leu Gln Ser Trp Cys Glu Lys Leu Ala Glu Ile Ile Trp Gln
         275             280             285

Asn Arg Gln Gln Ile Arg Arg Ala Glu His Leu Cys Gln Gln Leu Pro
     290             295             300

Ile Pro Gly Pro Val Glu Glu Met Leu Ala Glu Val Asn Ala Thr Ile
305             310             315                         320

Thr Asp Ile Ile Ser Ala Leu Val Thr Ser Thr Phe Ile Ile Glu Lys
             325             330             335

Gln Pro Pro Gln Val Leu Lys Thr Gln Thr Lys Phe Ala Ala Thr Val
             340             345             350

Arg Leu Leu Val Gly Gly Lys Leu Asn Val His Met Asn Pro Pro Gln
         355             360             365

Val Lys Ala Thr Ile Ile Ser Glu Gln Gln Ala Lys Ser Leu Leu Lys
     370             375             380

Asn Glu Asn Thr Arg Asn Glu Cys Ser Gly Glu Ile Leu Asn Asn Cys
385             390             395                         400

Cys Val Met Glu Tyr His Gln Ala Thr Gly Thr Leu Ser Ala His Phe
             405             410             415

Arg Asn Met Ser Leu Lys Arg Ile Lys Arg Ala Asp Arg Arg Gly Ala
             420             425             430

Glu Ser Val Thr Glu Glu Lys Phe Thr Val Leu Phe Glu Ser Gln Phe
             435             440             445

| | | | | | | | | | | | | | | |
|---|---|---|---|---|---|---|---|---|---|---|---|---|---|---|
| Ser | Val | Gly | Ser | Asn | Glu | Leu | Val | Phe | Gln | Val | Lys | Thr | Leu | Ser | Leu |
| | 450 | | | | 455 | | | | | 460 | | | | |
| Pro | Val | Val | Val | Ile | Val | His | Gly | Ser | Gln | Asp | His | Asn | Ala | Thr | Ala |
| 465 | | | | | 470 | | | | | 475 | | | | | 480 |
| Thr | Val | Leu | Trp | Asp | Asn | Ala | Phe | Ala | Glu | Pro | Gly | Arg | Val | Pro | Phe |
| | | | | 485 | | | | | 490 | | | | | 495 | |
| Ala | Val | Pro | Asp | Lys | Val | Leu | Trp | Pro | Gln | Leu | Cys | Glu | Ala | Leu | Asn |
| | | | 500 | | | | | 505 | | | | | 510 | | |
| Met | Lys | Phe | Lys | Ala | Glu | Val | Gln | Ser | Asn | Arg | Gly | Leu | Thr | Lys | Glu |
| | | 515 | | | | | 520 | | | | | 525 | | | |
| Asn | Leu | Val | Phe | Leu | Ala | Gln | Lys | Leu | Phe | Asn | Asn | Ser | Ser | Ser | His |
| | 530 | | | | | 535 | | | | | 540 | | | | |
| Leu | Glu | Asp | Tyr | Ser | Gly | Leu | Ser | Val | Ser | Trp | Ser | Gln | Phe | Asn | Arg |
| 545 | | | | | 550 | | | | | 555 | | | | | 560 |
| Glu | Asn | Leu | Pro | Gly | Trp | Asn | Tyr | Thr | Phe | Trp | Gln | Trp | Phe | Asp | Gly |
| | | | | 565 | | | | | 570 | | | | | 575 | |
| Val | Met | Glu | Val | Leu | Lys | Lys | His | His | Lys | Pro | His | Trp | Asn | Asp | Gly |
| | | | 580 | | | | | 585 | | | | | 590 | | |
| Ala | Ile | Leu | Gly | Phe | Val | Asn | Lys | Gln | Gln | Ala | His | Asp | Leu | Leu | Ile |
| | | 595 | | | | | 600 | | | | | 605 | | | |
| Asn | Lys | Pro | Asp | Gly | Thr | Phe | Leu | Leu | Arg | Phe | Ser | Asp | Ser | Glu | Ile |
| | 610 | | | | | 615 | | | | | 620 | | | | |
| Gly | Gly | Ile | Thr | Ile | Ala | Trp | Lys | Phe | Asp | Ser | Pro | Glu | Arg | Asn | Leu |
| 625 | | | | | 630 | | | | | 635 | | | | | 640 |
| Trp | Asn | Leu | Lys | Pro | Phe | Thr | Thr | Arg | Asp | Phe | Ser | Ile | Arg | Ser | Leu |
| | | | | 645 | | | | | 650 | | | | | 655 | |
| Ala | Asp | Arg | Leu | Gly | Asp | Leu | Ser | Tyr | Leu | Ile | Tyr | Val | Phe | Pro | Asp |
| | | | 660 | | | | | 665 | | | | | 670 | | |
| Arg | Pro | Lys | Asp | Glu | Val | Phe | Ser | Lys | Tyr | Tyr | Thr | Pro | Val | Leu | Ala |
| | | 675 | | | | | 680 | | | | | 685 | | | |
| Lys | Ala | Val | Asp | Gly | Tyr | Val | Lys | Pro | Gln | Ile | Lys | Gln | Val | Val | Pro |
| | 690 | | | | | 695 | | | | | 700 | | | | |
| Glu | Phe | Val | Asn | Ala | Ser | Ala | Asp | Ala | Gly | Gly | Ser | Ser | Ala | Thr | Tyr |
| 705 | | | | | 710 | | | | | 715 | | | | | 720 |
| Met | Asp | Gln | Ala | Pro | Ser | Pro | Ala | Val | Cys | Pro | Gln | Ala | Pro | Tyr | Asn |
| | | | | 725 | | | | | 730 | | | | | 735 | |
| Met | Tyr | Pro | Gln | Asn | Pro | Asp | His | Val | Leu | Asp | Gln | Asp | Gly | Glu | Phe |
| | | | 740 | | | | | 745 | | | | | 750 | | |
| Asp | Leu | Asp | Glu | Thr | Met | Asp | Val | Ala | Arg | His | Val | Glu | Glu | Leu | Leu |
| | | 755 | | | | | 760 | | | | | 765 | | | |
| Arg | Arg | Pro | Met | Asp | Ser | Leu | Asp | Ser | Arg | Leu | Ser | Pro | Pro | Ala | Gly |
| | 770 | | | | | 775 | | | | | 780 | | | | |
| Leu | Phe | Thr | Ser | Ala | Arg | Gly | Ser | Leu | Ser | | | | | | |
| 785 | | | | | 790 | | | | | | | | | | |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GTATTTCCCA GAAAAGGAAC      20

(2) INFORMATION FOR SEQ ID NO:4:

(i) SEQUENCE CHARACTERISTICS:
     (A) LENGTH: 20 base pairs
     (B) TYPE: nucleic acid
     (C) STRANDEDNESS: single
     (D) TOPOLOGY: linear (ii) MOLECULE TYPE: cDNA (xi) SEQUENCE DESCRIPTION: SEQ ID NO:4:

GTATCACCCA GTCAAGGAAC　　　　　　　　　　　　　　　　　　　　　　　　　　　　20